United States Patent
Padovani

(10) Patent No.: US 10,285,861 B2
(45) Date of Patent: May 14, 2019

(54) SKI GOGGLES HAVING A LARGE FIELD OF VISION

(71) Applicant: Carl Zeiss Vision Italia S.p.A., Castiglione Olona-Varese (IT)

(72) Inventor: Roberto Padovani, Malnate (IT)

(73) Assignee: Carl Zeiss Vision Italia S.p.A., Castiglione Olona-Varese (IT)

(*) Notice: Subject to any disclaimer, the term of this patent is extended or adjusted under 35 U.S.C. 154(b) by 0 days.

(21) Appl. No.: 14/672,382

(22) Filed: Mar. 30, 2015

(65) Prior Publication Data
US 2015/0272783 A1    Oct. 1, 2015

(30) Foreign Application Priority Data

Mar. 28, 2014  (AT) .............................. GM50047/2014
Mar. 28, 2014  (DE) .................... 20 2014 002 708 U

(51) Int. Cl.
*A61F 9/02*        (2006.01)

(52) U.S. Cl.
CPC ................. *A61F 9/02* (2013.01); *A61F 9/028* (2013.01)

(58) Field of Classification Search
CPC . A61F 9/02; A61F 9/026; A61F 9/027; A63B 33/002; B63C 11/12
See application file for complete search history.

(56) References Cited

U.S. PATENT DOCUMENTS

| | | | | |
|---|---|---|---|---|
| 2,537,047 A * | 1/1951 | Gatten | ..................... | G02C 7/02 351/159.02 |
| 3,950,082 A * | 4/1976 | Volk | ..................... | B24B 13/065 351/159.41 |
| 4,176,410 A * | 12/1979 | Matthias | ................. | A61F 9/026 2/436 |
| 4,556,995 A | 12/1985 | Yamamoto | | |
| 5,478,824 A * | 12/1995 | Burns | ................. | C08G 18/758 351/159.48 |
| 5,495,303 A * | 2/1996 | Kolentsi | ................. | A61F 9/026 2/428 |

(Continued)

FOREIGN PATENT DOCUMENTS

| | | |
|---|---|---|
| DE | 24 08 982 A1 | 9/1975 |
| DE | 87 09 530 U1 | 12/1987 |

(Continued)

OTHER PUBLICATIONS

English translation and the Search Report of the German Patent Office dated Jan. 16, 2015 in German patent application 20 2014 002 708.0 on which the claim of priority is based.

(Continued)

*Primary Examiner* — Sally Haden
(74) *Attorney, Agent, or Firm* — Walter Ottesen, P.A.

(57) ABSTRACT

Ski goggles for a goggles wearer have a frame and a goggle lens supported by the frame. The goggle lens has a surface facing the wearer's face during normal use and has a surface facing away from the wearer's face. A frame pad is connected to the frame and is seated on the wearer's face during normal use. A retaining strap holds the ski goggles on the wearer's head during normal use. The frame has a thickness ($d_1$, $d_2$) of less than 1.5 centimeters in a perpendicular direction to the surface of the lens facing the wearer's face during normal use.

14 Claims, 2 Drawing Sheets

(56) References Cited

U.S. PATENT DOCUMENTS

| | | | |
|---|---|---|---|
| 5,495,623 A * | 3/1996 | Leonardi | A61F 9/026 2/431 |
| 5,790,230 A | 8/1998 | Sved | |
| 2001/0033363 A1* | 10/2001 | Chateau | G02C 7/041 351/216 |
| 2001/0035935 A1* | 11/2001 | Bhalakia | B29D 11/00028 351/159.62 |
| 2002/0067463 A1* | 6/2002 | Obara | G02C 7/02 351/159.07 |
| 2003/0030771 A1* | 2/2003 | Hursey, Jr. | A61F 11/12 351/123 |
| 2004/0117898 A1* | 6/2004 | Penque, Jr. | A61F 9/028 2/431 |
| 2006/0117449 A1* | 6/2006 | Hahn | A42B 3/20 2/9 |
| 2007/0024806 A1* | 2/2007 | Blanshay | G02C 9/00 351/62 |
| 2008/0055538 A1 | 3/2008 | Kobayashi et al. | |
| 2009/0100577 A1* | 4/2009 | Kobayashi | A61F 9/02 2/436 |
| 2011/0258758 A1* | 10/2011 | Renaud-Goud | A61F 9/027 2/427 |
| 2011/0258759 A1* | 10/2011 | Renaud-Goud | A61F 9/026 2/428 |
| 2011/0258760 A1* | 10/2011 | Renaud-Goud | A61F 9/027 2/431 |
| 2014/0063438 A1* | 3/2014 | Cater | A61F 9/028 351/62 |
| 2015/0272783 A1* | 10/2015 | Padovani | A61F 9/02 2/436 |
| 2015/0272784 A1* | 10/2015 | Padovani | A61F 9/029 2/436 |
| 2016/0008174 A1* | 1/2016 | Padovani | A61F 9/025 2/439 |

FOREIGN PATENT DOCUMENTS

| | | |
|---|---|---|
| DE | 94 04 037 U1 | 5/1994 |
| WO | 2007/053522 A2 | 5/2007 |

OTHER PUBLICATIONS

English translation and the Search Report of the Austrian Patent Office dated Jan. 28, 2015 in Austrian patent application GM 50047/2014-1,2 on which the claim of priority is based.

* cited by examiner

SKI GOGGLES HAVING A LARGE FIELD OF VISION

CROSS REFERENCE TO RELATED APPLICATIONS

This application claims priority of German patent application no. 20 2014 002 708.0, filed Mar. 28, 2014, and Austrian patent application no. GM50047/2014, filed Mar. 28, 2014, and the entire contents of both are incorporated herein by reference.

BACKGROUND OF THE INVENTION

A multiplicity of embodiments of ski goggles is known. The present invention is based on ski goggles for a goggles wearer, with a frame, with a goggle lens which is supported by the frame and has a surface facing the goggles wearer's face during normal use and having a surface facing away from the goggles wearer's face during normal use, with a frame pad which is connected to the frame and can be brought to rest on the goggles wearer's face, and with a retaining strap of the ski goggles on the goggles wearer's head. Ski goggles of this type are described, for example, in DE 87 09 530 U1 and U.S. Pat. No. 4,556,995.

Within the context of the present invention, the frame is understood as meaning only those parts which serve directly as a support of the goggle lens. Any components which do not support the goggle lens and are fastened to the support and serve, for example, as mountings for further accessories or for aesthetic purposes are not considered as belonging to the frame. In addition, components which are connected to the support, optionally even in a material coordinated therewith and which are located further than 1.5 cm away from the edge of the goggle lens in the region of the temples and serve, for example, merely for fastening the retaining strap, are not considered as being assigned to the frame.

The frame is generally composed of a plastic preferably having a certain degree of elasticity. The frame generally completely frames the outer edge of the goggle lens. The frame is generally curved concavely in a manner matched to the curvature of the goggles wearer's face.

Within the context of the present invention, a goggle lens is considered to be the transparent element through which the goggles wearer looks during normal use and which determines the field of view of the goggles wearer. The goggle lens may be composed of a plastic. The goggle lens may also be formed flexibly. The goggle lens may optionally also have a (possibly prescribed) dioptric effect. However, the goggle lens may also be formed as a lens not having a dioptric effect. The goggle lens is generally formed as a single piece and is provided for both eyes to look through.

The frame pad generally consists of a foam material having an elasticity which is increased in relation to the housing in order to be able to be adapted to the goggles wearer's face contour. There is generally an adhesive connection between frame and frame pad.

The retaining strap generally consists of a length-adjustable textile or rubber strap. The retaining strap is generally fastened to the frame. However, the retaining strap may also be fastened to the goggle lens.

The field of view, that is, the three-dimensional angular region through which the goggles wearer's eyes can see, is restricted by the goggles frame because of the above-described structural design of the ski goggles. In particular, the lateral and vertical view is restricted by the goggles frame. The ski goggles have to be of a certain thickness in order to ventilate the space between the goggle lens and goggles wearer's face so that the goggle lens does not mist up.

Although the above-described ski goggles have basically proven successful, there is a need for a large field of view which is less restricted or is not restricted at all by the frame of the goggle lens.

SUMMARY OF THE INVENTION

It is therefore an object of the invention to provide ski goggles with a greater field of view than ski goggles of a conventional type.

The ski goggles according to the invention have a frame, a goggle lens which is supported by the frame and has a surface facing the goggles wearer's face during normal use and a surface facing away from the goggles wearer's face. The ski goggles according to the invention furthermore have a frame pad which is connected to the frame and is seated on the goggles wearer's face during normal use. Finally, the ski goggles have a retaining strap in order to hold the ski goggles on the goggles wearer's head. In a departure from the conventional type of ski goggles of the type in question and which are described in the introductory part of the description, the thickness of the frame is reduced. Specifically, in a perpendicular direction to that surface of the goggle lens which faces the goggles wearer's face during normal use, the frame has a thickness of less than 1.5 cm.

The effect which is therefore achieved is that the goggle lens is located very close to the goggles wearer's eye in the use position. This increases the viewing angle both in a vertical direction and in a horizontal direction. The reduction of the distance of the goggle lens from the eye is the key element for increasing the field of view for the goggles wearer. The object stated at the beginning is therefore fully achieved.

It has proven advantageous if the thickness of the frame is even less than 1.4 cm, furthermore preferably less than 1.3 cm. The distance between eye and goggle lens is therefore further reduced and the field of view further enlarged.

The thickness of the frame can generally not be reduced arbitrarily. Experimental investigations have revealed that adequate stability of the frame is achieved while ensuring that the goggle lens is supported if the thickness is selected to be greater than 0.2 cm, preferably greater than 0.3 cm, furthermore preferably greater than 0.4 cm.

The frame can have openings provided for ventilation. In the perpendicular direction to the surface facing the goggles wearer's face during normal use, the openings are arranged between the goggle lens and the frame pad. The ventilation openings permit a direct supply of air to the rear side of the goggle lens without further filtering, which effectively prevents misting up. The diameter of the preferably cylindrical openings is only between $1/20$ and $1/5$ of the thickness of the frame. There are preferably between 20 and 200 openings.

The ventilation openings can run parallel to that surface of the goggle lens which faces the goggles wearer's face during normal use. It is also possible for the ventilation openings to run in a vertical direction during normal use. When arranged appropriately, the ventilation openings can permit air to enter from below into the cavity between goggle lens and face and to exit upwards out of the cavity.

The design of ski goggles according to the invention has been specially adapted to the reduced thickness. The goggle lens can be formed spherically. In this case, the goggle lens has a basic curve of between 5 dpt and 6.5 dpt. The flatter curvature of the goggle lens is referred to as the basic curve.

In the case of minus lenses, the basic curve lies on the front side of the goggle lens; by contrast, in the case of plus lenses, the basic curve lies on the rear side facing the eye. If the goggle lens is formed torically, then a basic curve of preferably between 5 dpt and 6.5 dpt, the basic curve running in a horizontal direction during normal use, and a basic curve of between 2 dpt and 5 dpt, the basic curve running in a vertical direction, are selected.

The frame is preferably formed as a single part or in two parts in order to keep the manufacturing thereof cost-effective.

The frame can be at least partially composed of a flexible plastic with a modulus of elasticity of between 1 N/mm$^2$ and 500 N/mm$^2$. Ski goggles with elasticity of this type have proven particularly pleasant for the goggles wearer to wear because of the reduced thickness of the frame.

Not only is the frame crucial for the wearing comfort, but so too to a particular extent is the elasticity of the frame pad. Wearing trials have revealed that it is advantageous if the frame pad is at least partially composed of a flexible foam with a modulus of elasticity of between 0.02 N/mm$^2$ and 2 N/mm$^2$.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
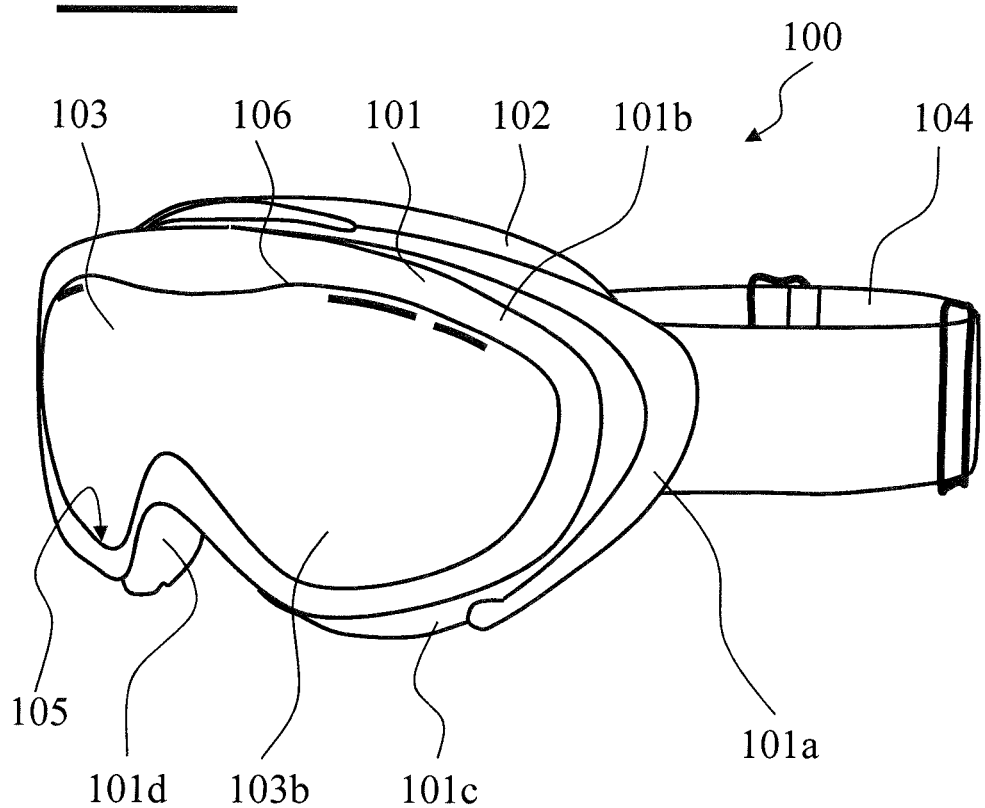
FIG. 1 shows an embodiment of ski goggles according to the invention in a three-dimensional perspective illustration.
Figure 2:
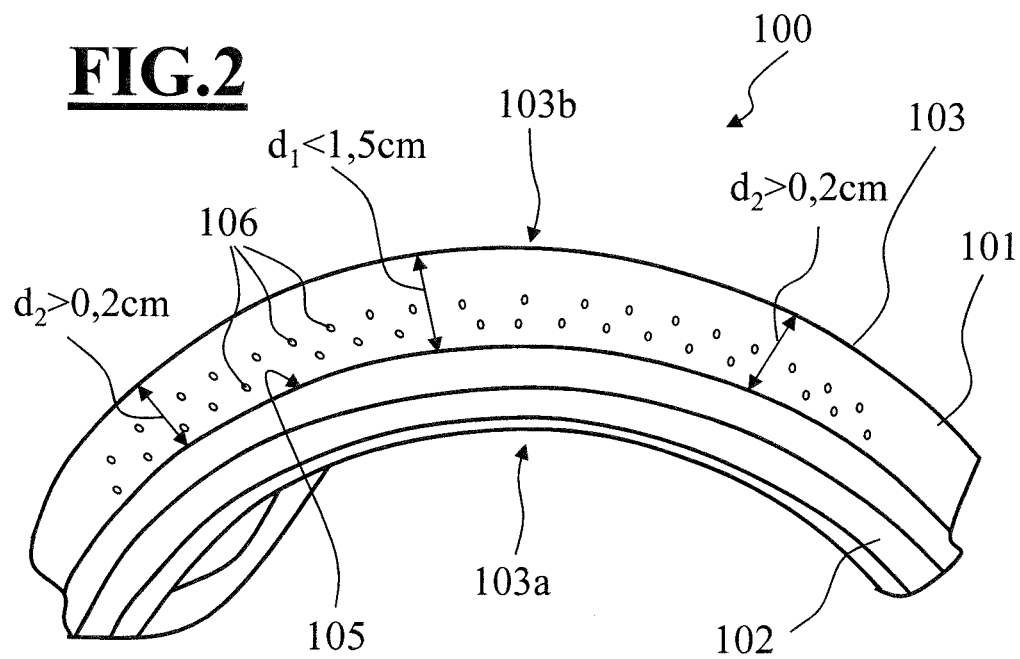
FIG. 2 shows the ski goggles according to FIG. 1 in plan view from above.

The ski goggles 100 shown in FIG. 1 and FIG. 2 have a frame 101, a frame pad 102, a goggle lens 103 and a retaining strap 104.

The goggle lens 103 is supported by the frame 101. For this purpose, the frame 101 has an encircling groove 105 into which the goggle lens 103 is inserted over the entire outer extent of the frame. The frame 101 is formed as a single piece and of the same material and is composed of polyurethane. The frame 101 is configured in the form of an elongated housing consisting of a slightly convexly curved upper part 101b and a lower part 101c, which forms a bent-in nose portion 101d.

The goggle lens 103 supported by the frame 101 has a surface 103a facing the goggles wearer's face during normal use and a surface 103b facing away from the goggles wearer's face during normal use. In the present embodiment, the goggle lens 103 is manufactured from polycarbonate or polyamide.

The frame pad 102 is adhesively bonded to that side of the frame 101 which faces the goggles wearer's face. The adhesive layer bears the reference numeral 105. The frame pad 102 is brought to rest on the goggles wearer's face during normal use. The frame pad 102 is composed of a soft foam. The foam is of an open-pore type which is preferred in respect of the permeability and capability of storing moisture. The face-side frame pad 102 has a lower density than that of the frame 101.

Frame 101 and frame pad 102 have a concave curvature taking into account the shape of a head.

The retaining strap 104, which holds the ski goggles 100 on the goggles wearer's head during normal use, is fastened to the rearwardly pointing part 101a of the frame 101. The retaining strap 104 is composed of a textile fabric. The retaining strap 104 is length-adjustable.

In a perpendicular direction to that surface 103a of the goggle lens 103, which faces the goggles wearer's face during normal use, the frame 101 has a thickness $d_1$ of approximately 1.4 cm in the center of the upper part 101b, the thickness steadily decreasing outwards towards the edge of the upper part 101b to a value $d_2$ of approximately 1.2 cm. In the perpendicular direction to the surface 103a facing the goggles wearer's face during normal use, the frame 101 has ventilation openings 106 arranged between the goggle lens 103 and the frame pad 102. In the embodiment presented, the ventilation openings 106 are configured as cylindrical bores with a bore diameter of approximately 0.8 mm. Two rows of 20 bores 106 in each case are introduced in a vertical direction into the upper part 101b of the frame 101. An identical number of bores 106 is located in a complementary arrangement in the lower part 101c of the frame 101.

The ski goggles 100 according to the invention of the present embodiment have a toric goggle lens 103 with a basic curve of 6.5 dpt in a horizontal direction and a basic curve of 5 dpt in a vertical direction.

Figure 3:
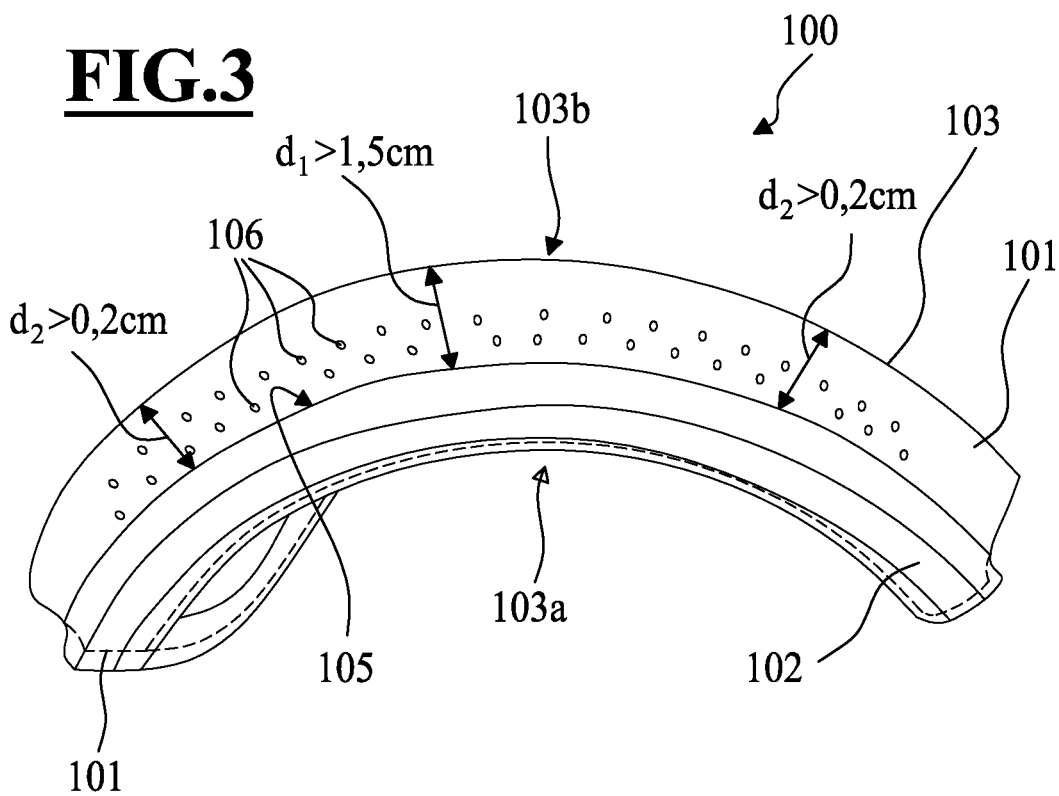
FIG. 3 is a rear elevation view of the ski goggles of FIG. 1.

FIG. 3 shows a rear elevation view of the ski goggles 100 of FIG. 1. As shown in FIG. 3, the goggle frame pad 102 extends over the entirety of the perimeter of the frame back side of the frame 101.

It is understood that the foregoing description is that of the preferred embodiments of the invention and that various changes and modifications may be made thereto without departing from the spirit and scope of the invention as defined in the appended claims.

What is claimed is:

1. Ski goggles for a goggles wearer, the ski goggles comprising:

a goggle lens defining a lens perimeter;

a goggle frame configured to support said goggle lens;

said goggle lens having a first surface adapted to face toward a face of the goggles wearer during normal use and a second surface adapted to face away from the face of the goggles wearer during normal use;

said goggle frame having a frame back side defining a perimeter and being configured to face the face of the goggles wearer during normal use;

a goggle frame pad defining a peripheral contact surface and being connected to said goggle frame over said perimeter of said frame back side of said goggle frame;

said goggle frame surrounding the entirety of said lens perimeter;

said goggle frame pad being configured to be seated on the face of the goggles wearer during normal use so as to cause said peripheral contact surface to be in contact engagement with the face of the goggles wearer;

a retaining strap configured to hold the ski goggles on a head of the goggles wearer during normal use;

said goggle frame having a center and left and right lateral edges;

said goggle frame having, in a direction perpendicular to said first surface, a first thickness ($d_1$) approximately at said center tapering down to a second thickness ($d_2$) toward said lateral edges with said first thickness ($d_1$) being greater than said second thickness ($d_2$); and, said first and second thicknesses ($d_1$, $d_2$) lying in a range between 0.2 centimeters and 1.5 centimeters.

2. The ski goggles of claim 1, wherein said first and second thicknesses ($d_1$, $d_2$) in said direction perpendicular to said first surface is less than 1.4 centimeters.

3. The ski goggles of claim 1, wherein said first and second thicknesses ($d_1$, $d_2$) in said direction perpendicular to said first surface is less than 1.3 centimeters.

4. The ski goggles of claim 1, wherein said first and second thicknesses ($d_1$, $d_2$) in said direction perpendicular to said first surface is greater than 0.3 centimeters.

5. The ski goggles of claim 1, wherein said first and second thicknesses ($d_1$, $d_2$) in said direction perpendicular to said first surface is greater than 0.4 centimeters.

6. The ski goggles of claim 1, wherein said goggle frame has a plurality of ventilation openings arranged between said goggle lens and said goggle frame pad in said direction perpendicular to said first surface.

7. The ski goggles of claim 6, wherein said ventilation openings run parallel to said first surface or said ventilation openings are adapted to run in a vertical direction during normal use.

8. The ski goggles of claim 1, wherein said goggle lens is spherical and has a base curve lying in a range of 5 diopters to 6.5 diopters.

9. The ski goggles of claim 1, wherein said goggle lens is toric and has a first base curve running horizontally when said ski goggles are in normal use and lying in a range of 5 diopters to 6.5 diopters and a second base curve running vertically lying in a range of 2 diopters to 5 diopters.

10. The ski goggles of claim 1, wherein said frame is a single component part or a two component part.

11. The ski goggles of claim 1, wherein said frame is made at least partially of a flexible plastic having a modulus of elasticity lying in a range of 2 newton/millimeter$^2$ to 100 newton/millimeter$^2$.

12. The ski goggles of claim 1, wherein said goggle frame pad is at least partially made of elastic foam material having a modulus of elasticity greater than 0.02 newton/millimeter$^2$.

13. Ski goggles for a goggles wearer, the ski goggles comprising:
a goggle lens defining a lens perimeter;
a goggle frame having a first lateral side and a second lateral side and being configured to support said goggle lens;
said goggle lens extending uninterruptedly from said first lateral side to said second lateral side of said goggle frame;
said goggle lens having a first surface adapted to a face of the goggles wearer during normal use and a second surface adapted to face away from the face of the goggles wearer during normal use;
a goggle frame pad defining a peripheral contact surface and being connected to said goggle frame;
said goggle frame surrounding the entirety of said lens perimeter;
said goggle frame having a frame back side defining a perimeter and being configured to be directed toward the face of the goggles wearer during normal use;
said goggle frame pad being configured to be seated on the face of the goggles wearer during normal use so as to cause said peripheral contact surface to be in contact engagement with the face of the goggles wearer;
said goggle frame pad extending over the entirety of said perimeter of said frame back side and being adapted to be in snug contact engagement with the face of the goggles wearer;
a retaining strap configured to hold the ski goggles on a head of the goggles wearer during normal use;
said goggle frame having a center and left and right lateral edges;
said goggle frame having, in a direction perpendicular to said first surface, a first thickness ($d_1$) approximately at said center tapering down to a second thickness ($d_2$) toward said lateral edges with said first thickness ($d_1$) being greater than said second thickness ($d_2$); and,
said first and second thicknesses ($d_1$, $d_2$) lying in a range between 0.2 centimeters and 1.5 centimeters.

14. Ski goggles for a goggles wearer, the ski goggles comprising:
a goggle lens defining a lens perimeter;
a goggle frame configured to support said goggle lens;
said goggle lens having a first surface adapted to face a face if the goggles wearer during normal use and a second surface adapted to face away from the face of the goggles wearer during normal use;
a goggle frame pad defining a peripheral contact surface and being connected to said goggle frame;
said goggle frame surrounding the entirety of said lens perimeter;
said goggle frame having a frame back side defining a perimeter and being configured to be directed toward the face of the goggles wearer during normal use;
said goggle frame pad being configured to be seated on the face of the goggles wearer during normal use so as to cause said peripheral contact surface to be in contact engagement with the face of the goggles wearer;
said goggle frame pad extending over the entirety of said perimeter of said frame back side and being adapted to be in snug contact engagement with the face of the goggle wearer along said perimeter so as to generate a seal between said goggle frame and the face of the goggles wearer during normal use;
a retaining strap configured to hold the ski goggles on a head of the goggles wearer during normal use;
said goggle frame having a center and left and right lateral edges;
said goggle frame having, in a direction perpendicular to said first surface, a first thickness ($d_1$) approximately at said center tapering down to a second thickness ($d_2$) toward said lateral edges with said first thickness ($d_1$) being greater than said second thickness ($d_2$); and,
said first and second thickness ($d_1$, $d_2$) lying in a range between 0.2 centimeters and 1.5 centimeters.

* * * * *